US00PP31268P2

(12) United States Plant Patent
Danziger

(10) Patent No.: US PP31,268 P2
(45) Date of Patent: Dec. 24, 2019

(54) ***LEUCANTHEMUM* PLANT NAMED 'DLEULUCCHI'**

(50) Latin Name: *Leucanthemum superbum*
Varietal Denomination: DLEULUCCHI

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 15/998,202

(22) Filed: Jul. 12, 2018

(51) Int. Cl.
*A01H 5/02* (2018.01)
*A01H 6/14* (2018.01)

(52) U.S. Cl.
USPC ..... Plt./285
CPC ..... *A01H 6/14* (2018.05)

(58) Field of Classification Search
USPC ..... Plt./285
See application file for complete search history.

*Primary Examiner* — Anne Marie Grunberg
(74) *Attorney, Agent, or Firm* — Cassandra Bright

(57) ABSTRACT

A new and distinct cultivar of *Leucanthemum superbum* hybrid plant named 'DLEULUCCHI' is disclosed, characterized by a very compact, plant form. Plants begin flowering early and do not require vernalization. The new variety is a *Leucanthemum superbum* hybrid plant, and naturally blooms from Spring to Fall.

2 Drawing Sheets

Latin name of the genus and species: *Leucanthemum superbum.*

Variety denomination: 'DLEULUCCHI'.

BACKGROUND OF THE INVENTION

The new cultivar is a product of a planned breeding program conducted by the inventor, Gavriel Danziger in Moshav Mishmar Hashiva, Israel. The objective of the breeding program was to produce new *Leucanthemum* varieties with compact plant habits, good heat tolerance and not requiring vernalization. The open-pollination resulting in this new variety was made during November of 2013.

Asexual reproduction of the new cultivar 'DLEULUCCHI' was first performed by basal vegetative cuttings in April of 2014, at a greenhouse in Moshav Mishmar Hashiva, Israel. All subsequent propagation has shown that the unique features of this cultivar are stable and reproduced true to type in successive generations.

SUMMARY OF THE INVENTION

The cultivar has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DLEULUCCHI' These characteristics in combination distinguish 'DLEULUCCHI' as a new and distinct *Leucanthemum* cultivar:

1. Very early blooming
2. Vernalization not required.
3. Very compact plant habit.

4. Good heat tolerance.
5. Good rooting performance.

PARENT COMPARISON

Plants of the new cultivar 'DLEULUCCHI' are similar to plants of the parent variety, *Leucanthemum* 'LK-9-19' in most horticultural characteristics. Plants of 'DLEULUCCHI', however, differ in the following:

1. The new variety has a much more compact and dense plant habit than the seed parent.
2. Overall plant size of the new variety is smaller than the seed parent.

COMMERCIAL COMPARISON

Plants of the new cultivar 'DLEULUCCHI' are similar to plants of the commercial variety *Leucanthemum* 'Snowcap', unpatented, in most horticultural characteristics. However, plants of the new cultivar 'DLEULUCCHI' differ in the following:

1. The new variety does not require vernalization to induce flowering, 'Snow Cap' requires vernalization.
2. Plants of 'DLEULUCCHI' are much more compact than plants of 'Snow Cap'.

BRIEF DESCRIPTION OF THE PHOTOGRAPHS

Figure 1:
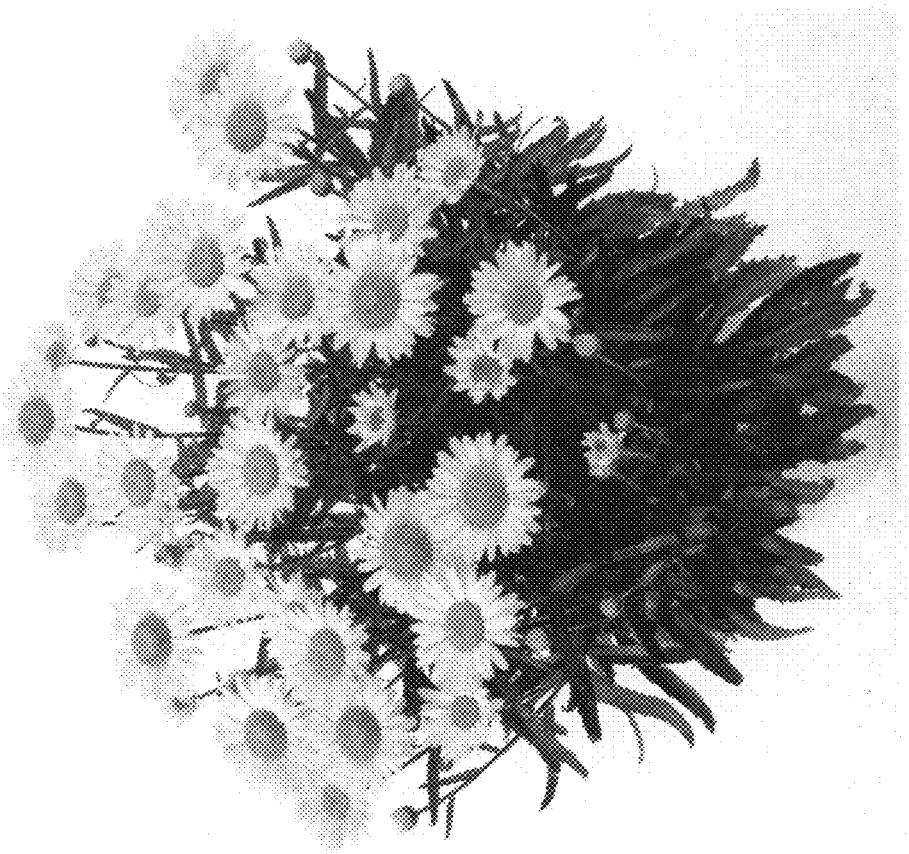

The accompanying photograph in FIG. 1 illustrates in full color a typical plant of 'DLEULUCCHI' grown in a greenhouse. The pot size is a commercial 12 cm container. The plant shown is approximately 20 weeks old.

Figure 2:
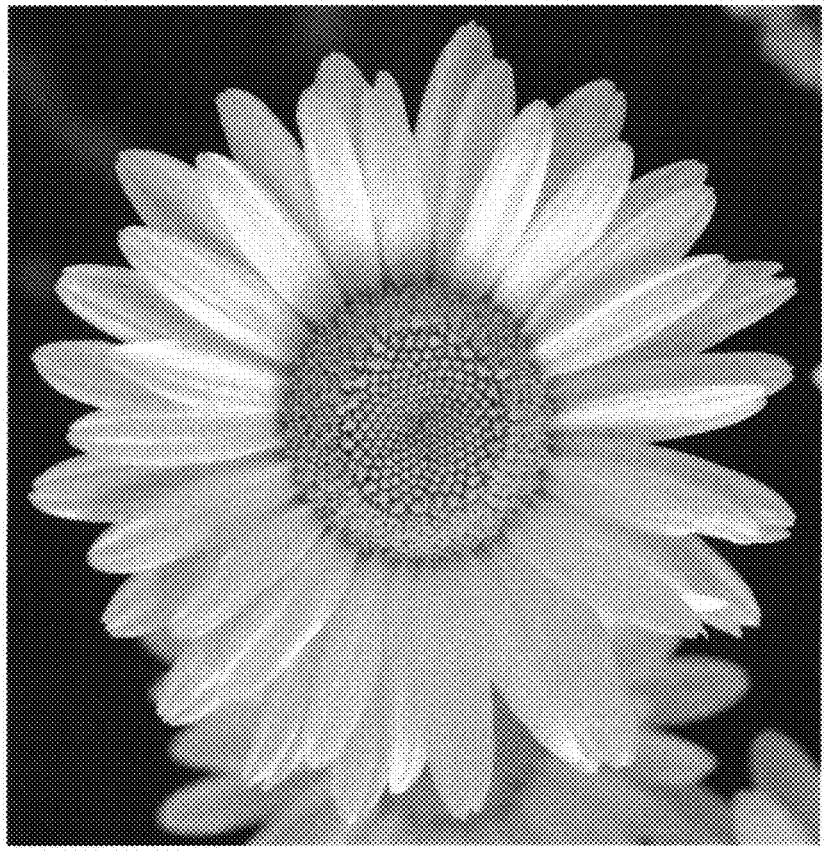

FIG. 2 illustrates a close-up view of the inflorescence.

The photographs were taken using conventional techniques and although colors may appear different from actual colors due to light reflectance it is as accurate as possible by conventional photographic techniques.

DETAILED BOTANICAL DESCRIPTION

General growing conditions of plant described:
Greenhouse/nursery/outdoors: Outdoors.
Temperature range: About 20° C. to 35° C. during the day, about 15° C. to 20° C. night.
City and country: Moshav Mishmar Hashiva, Israel.
Time of year: Spring.
Chemical treatments, including growth regulators: None.
Age of plant described: About 120 days from a rooted cutting.
Botanical classification: *Leucanthemum superbum* 'DLEULUCCHI'.

PROPAGATION

Time to rooting: 20 days at approximately 16° C.
Root description: Strong, long woody roots with fibrous secondary roots. Roots color brown, not accurately measured with the R.H.S. chart.

PLANT

Growth habit: Compact hardy flowering perennial.
Height: Approximately 35 cm.
Plant spread: Approximately 40 cm.
Branching characteristics: Abundant basal branching.
Length of lateral branches: Approximately 25-30 cm.
Diameter of lateral branches: Approximately 0.3 cm.
Texture of lateral branches: Smooth.
Internode length: Approximately 3 cm.
Strength of lateral branches: Strong, not easily broken, wiry.
Color of lateral branches: Near RHS 144A.
Aspect/angle of branches: Straight, approximately 25 to 45 degrees from center.
Number of leaves per lateral branch: Approximately 4-5 pairs.

FOLIAGE

Leaf:
- *Arrangement*.—Sub-opposite (not exactly one across from the other).
- *Average length*.—Approximately 10 cm.
- *Average width*.—Approximately 1.5 cm.
- *Shape of blade*.—Oblanceolate.
- *Lobing*.—None.
- *Apex*.—Acute.
- *Base*.—Broad tapered.
- *Attachment*.—Sessile.
- *Margin*.—Moderately serrated.
- *Texture of top surface*.—Smooth.
- *Texture of bottom surface*.—Smooth.
- *Appearance* (*ie: shiny, metallic, matte*) *top surface*.—Shiny.
- *Appearance bottom surface*.—Lighter in color.
- *Leaf internode length*.—Approximately 3 cm.
- *Color*.—Young foliage upper side: Near RHS Green 137A. Young foliage under side: Near RHS Green 137C. Mature foliage upper side: Near RHS Green 137A. Mature foliage under side: Near RHS Green 137C.
- *Venation*.—Type: One central running from base to tip. Venation color upper side: Near RHS Green 137A. Venation color under side: Near RHS Green 137C.

Petiole: None.

FLOWER

Bud:
- *Bud shape*.—Globular, somewhat flattened.
- *Bud length*.—Approximately 0.7 cm.
- *Bud diameter*.—Approximately 1.2 cm.
- *Bud color*.—Near RHS Green 137C.

Inflorescence:
- *Form*.—Daisy-type inflorescence form with oblanceolate-shaped ray florets. Inflorescences positioned above and beyond the foliage; inflorescences terminal and axillary. Disc and ray florets developing acropetally on a capitulum. Inflorescences face mostly upright to outward.

Flower:
- *Diameter of entire flower*.—Approximately 5-5.5 cm.
- *Depth of flower*.—Approximately 0.8 cm.
- *Width of disc*.—Approximately 2-2.5 cm.
- *Depth of disc*.—Approximately 0.5 cm.

Ray florets:
- *Number of ray florets*.—Average range 24 to 36.
- *Length*.—Approximately 2.5 cm.
- *Width*.—Approximately 0.5 cm.
- *Apex shape*.—Rounded.
- *Margin*.—Smooth.
- *Color*.—Upper surface at first opening: Near RHS White 155C. Upper surface at maturity: Near RHS White 155C. Upper surface at fading: Near RHS White 155C. Under surface at first opening: Near RHS White 155C. Under surface at maturity: Near RHS White 155C. Under surface at fading: Near RHS White 155C.

Disc florets:
- *Number of disc florets*.—Average range 220 to 250.
- *Length*.—Approximately 0.9 cm.
- *Width*.—Approximately 1 mm.
- *Shape*.—Tubular.
- *Margin*.—Entire.
- *Color*.—At first opening: Near RHS Yellow-Green 153C. At maturity: Near RHS Yellow-Green 153C. At fading: Near RHS Yellow-Green 153C.

Receptacle:
- *Shape*.—Convex.
- *Width*.—2-2.5 cm.
- *Depth*.—3 mm.
- *Color*.—Near 137C.

Fragrance: Musty.

Involucral bracts/phyllaries:
- *Number*.—Approximately 20.
- *Length*.—Approximately 1 cm.
- *Width*.—Approximately 0.3 cm.
- *Shape*.—Narrow deltate.
- *Texture*.—Smooth all surfaces.
- *Apex shape*.—Acute.
- *Margin*.—Smooth.

Peduncle:
- *Length*.—Approximately 16 cm.
- *Diameter*.—Approximately 0.3 cm.
- *Angle*.—Upright, straight.

*Color*.—Near RHS Yellow-Green 144A.
*Peduncle texture*.—Smooth.

REPRODUCTIVE ORGANS

Disc florets:
Androecium:
*Stamens*.—4.
*Anther shape*.—Cylindrical.
*Anther length*.—Approximately 0.5-1.0 mm.
*Anther color*.—Near RHS Yellow-Green 153C.
*Pollen quantity*.—Abundant.
*Pollen color*.—Near RHS Yellow 13B.
Gynoecium:
*Pistil number*.—1 per floret.
*Pistil shape*.—Two-parted.
*Pistil length*.—Approx. 0.2 cm.
*Style length*.—Approx. 0.1 cm.
*Style color*.—Near RHS Green 142A.
*Stigma shape*.—Less than 1 mm, irregular linear.
*Stigma color*.—Too small to accurately measure with R.H.S. chart.
*Ovary diameter*.—0.1 cm.
*Ovary color*.—Near RHS Green 142A.
Ray florets: Not present.

OTHER CHARACTERISTICS

Disease resistance: Neither resistance nor susceptibility to diseases or pests has been observed in this variety to date.
Drought tolerance and cold tolerance: Hardy perennial with good heat tolerance. Hardy to at least −2° C., high temperature tolerance to at least 38° C.
Fruit/seed production: Not observed.

What is claimed is:

1. A new and distinct cultivar of *Leucanthemum* plant named 'DLEULUCCHI' as herein illustrated and described.

* * * * *